United States Patent
Das et al.

(10) Patent No.: US 11,154,229 B2
(45) Date of Patent: Oct. 26, 2021

(54) METHOD AND SYSTEM FOR PRE-PROCESSING OF AN EEG SIGNAL FOR COGNITIVE LOAD MEASUREMENT

(71) Applicant: Tata Consultancy Services Limited, Mumbai (IN)

(72) Inventors: Rajat Kumar Das, Kolkata (IN); Aniruddha Sinha, Kolkata (IN); Debatri Chatterjee, Kolkata (IN); Shreyasi Datta, Kolkata (IN); Rahul Dasharath Gavas, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 690 days.

(21) Appl. No.: 15/765,763

(22) PCT Filed: Oct. 4, 2016

(86) PCT No.: PCT/IB2016/055914
§ 371 (c)(1),
(2) Date: Apr. 4, 2018

(87) PCT Pub. No.: WO2017/060804
PCT Pub. Date: Apr. 13, 2017

(65) Prior Publication Data
US 2018/0310851 A1    Nov. 1, 2018

(30) Foreign Application Priority Data
Oct. 5, 2015    (IN) .......................... 3778/MUM/2015

(51) Int. Cl.
*A61B 5/316*    (2021.01)
*A61B 5/00*    (2006.01)
(Continued)

(52) U.S. Cl.
CPC .............. *A61B 5/316* (2021.01); *A61B 5/291* (2021.01); *A61B 5/369* (2021.01); *A61B 5/374* (2021.01);
(Continued)

(58) Field of Classification Search
None
See application file for complete search history.

(56) References Cited

U.S. PATENT DOCUMENTS

| 5,447,166 A | 9/1995 | Gevins |
| 6,092,058 A | 7/2000 | Smyth |

(Continued)

FOREIGN PATENT DOCUMENTS

WO    WO-2014/059431    4/2014

OTHER PUBLICATIONS

Berka et al., "Real-Time Analysis of EEG Indexes of Alertness, Cognition, and Memory Acquired With a Wireless EEG Headset", 2004, International Journal of Human-Computer Interaction, 17(2), 151-170 (Year: 2004).*

*Primary Examiner* — Michael R Bloch
(74) *Attorney, Agent, or Firm* — Finnegan, Henderson, Farabow, Garrett & Dunner, LLP

(57) ABSTRACT

A method and system is provided for pre-processing of an electroencephalography (EEG) signal for cognitive load measurement. The present application provides a method and system for pre-processing of electroencephalography signal for cognitive load measurement of a user, comprises of capturing the electroencephalography signal from the head of the user, detecting the plurality of system artifacts in the captured electroencephalography signal, detecting and removing noisy window from the captured electroencephalography signal, detecting an eye blink region and filtering out said detected eye blink region from the captured elec- (Continued)

troencephalography signal, utilizing the filtered electroencephalography signal for measuring the cognitive load of the user and subsequently computing different levels of mental workloads on the user using variation of spatial distribution of frontal scalp EEG electrodes for measured cognitive load.

10 Claims, 6 Drawing Sheets

(51) Int. Cl.
  *A61B 5/291*  (2021.01)
  *A61B 5/369*  (2021.01)
  *A61B 5/374*  (2021.01)
  *A61B 5/377*  (2021.01)
  *A61B 5/16*  (2006.01)

(52) U.S. Cl.
  CPC ............ *A61B 5/377* (2021.01); *A61B 5/7203* (2013.01); *A61B 5/7207* (2013.01); *A61B 5/7221* (2013.01); *A61B 5/7282* (2013.01); *A61B 5/163* (2017.08)

(56) References Cited

U.S. PATENT DOCUMENTS

| | | |
|---|---|---|
| 2005/0273017 A1* | 12/2005 | Gordon ............... A61B 5/16 600/544 |
| 2007/0236488 A1 | 10/2007 | Mathan et al. |
| 2010/0332173 A1* | 12/2010 | Watson ............ A61B 5/02255 702/85 |
| 2013/0012789 A1 | 1/2013 | Horseman |
| 2013/0331727 A1 | 12/2013 | Zhang et al. |
| 2015/0038869 A1* | 2/2015 | Simon ............... A61B 5/377 600/544 |
| 2015/0088024 A1* | 3/2015 | Sackellares ......... A61B 5/4094 600/544 |
| 2015/0148700 A1 | 5/2015 | Mhuircheartaigh et al. |

* cited by examiner

METHOD AND SYSTEM FOR PRE-PROCESSING OF AN EEG SIGNAL FOR COGNITIVE LOAD MEASUREMENT

FIELD OF THE INVENTION

The present application generally relates to cognitive load measurement. Particularly, the application provides a method and system for pre-processing of an electroencephalography (EEG) signal for cognitive load measurement of a user.

BACKGROUND OF THE INVENTION

Electroencephalography (EEG) is typically a non-invasive method for monitoring brain activity, which is further utilized for measuring cognitive load of a user, as the brain is the source of cognitive activity. The assessment of cognitive load may have various applications, such as content generation, test various applications on electronic devices, and applications related to human interactions. In spite of having a variety of applications, EEG signals are very low amplitude signals and thus are very susceptible to various system artifacts, thereby exhibiting less accuracy while measuring cognitive load.

Prior art literature illustrates a variety of solutions for detection and removal of system artifacts in EEG signal. However, prior art literature has never explored pre-processing of the low resolution EEG signal contaminated with system artifacts, which can be further utilized for real-time signal analysis with low resolution devices Prior art literature discloses, an Independent component analysis (ICA) or adaptive filter based approaches are applied for filtering the EEG signal, wherein the eye blink region detection may not be required. However, the Independent component analysis (ICA) or adaptive filter based approaches are confined to high resolution systems (32 or 64 channel EEG device) having large number of electrodes. While on the other hand, for low resolution systems, such approaches results in less accurate results, as the separation between the leads are high. Some of the prior art rejects system artifact contaminated portion however such approach would result in substantial data loss. Furthermore, most of the approaches described in the prior art cannot be used in real-time signal analysis for measuring cognitive load.

Prior art literature discloses, an electroculogram based approach for detecting eye blinks by using extra electrodes placed close to eyes. The signals are amplified and then subtracted from the EEG signals to extract a clean signal. However the usage of an extra electrodes in BCI related application for mass usage is not a very practical solution. There are several approaches have been used to detect the eye blinks for a low resolution device. Prior art literature discloses an approach to use a numerical differentiation based method for detection of eye blinks. Another approach have used a correlation based method for automatic detection of eye blinks from EEG signals. Other approach is to detect eye blink from correlation between open and close eye images for example eye blink is detected by calculating eyelid's state detecting value. One of the approach have applied histogram back-projection and inner movement eyelid motion for detecting eye movements. Another approach can be Hilbert-Huang transform (HHT) which is used throughout the signal for this purpose. However the main disadvantage being, it changes the feature values for the non-blink regions as well.

Thus, in the light of the above mentioned background art, it is evident that, there is a need for a solution which is capable of pre-processing the EEG signals for the low resolution devices, which may be utilized to differentiate between different levels of the mental workload of a user, which makes these devices useful for non-medical brain computer interface applications requiring mass deployment. The pre-processing block removes the system artifacts from the low resolution EEG signals for cognitive load measurement.

Thereby, a method and system for pre-processing of EEG signals for cognitive load measurement is desired.

SUMMARY OF THE INVENTION

Before the present methods, systems, and hardware enablement are described, it is to be understood that this invention is not limited to the particular systems, and methodologies described, as there can be multiple possible embodiments of the present invention which are not expressly illustrated in the present disclosure. It is also to be understood that the terminology used in the description is for the purpose of describing the particular versions or embodiments only, and is not intended to limit the scope of the present invention which will be limited only by the appended claims.

The present application provides a method and system for pre-processing of an electroencephalography signal of a user for cognitive load measurement.

The present application provides a method and system (200) for pre-processing of an electroencephalography signal of a user for cognitive load measurement; said system (200) comprises of an electroencephalography signal recording device (202) adapted for capturing the electroencephalography signal of the user, wherein the electroencephalography signal is generated corresponding to a stimulus; an artifact detection module (204) adapted for detecting a plurality of system artifacts in the captured electroencephalography signal; a noisy window removal module (206) adapted for removing a noisy window from said electroencephalography signal; an eye blink region detection module (208) adapted for detecting an eye blink region in said electroencephalography signal; an eye blink region filtering module (210) adapted for filtering out said detected eye blink region from the electroencephalography signal for measuring the cognitive load of the user; and a cognitive load measurement module (212) adapted for utilizing filtered electroencephalography signal for measuring the cognitive load of the user and subsequently computing different levels of mental workloads on the user using variation of spatial distribution of frontal scalp EEG electrodes for measured cognitive load.

BRIEF DESCRIPTION OF THE DRAWINGS

The foregoing summary, as well as the following detailed description of preferred embodiments, are better understood when read in conjunction with the appended drawings. For the purpose of illustrating the invention, there is shown in the drawings exemplary constructions of the invention; however, the invention is not limited to the specific methods and system disclosed. In the drawings.

DETAILED DESCRIPTION OF THE INVENTION

Figure 1:
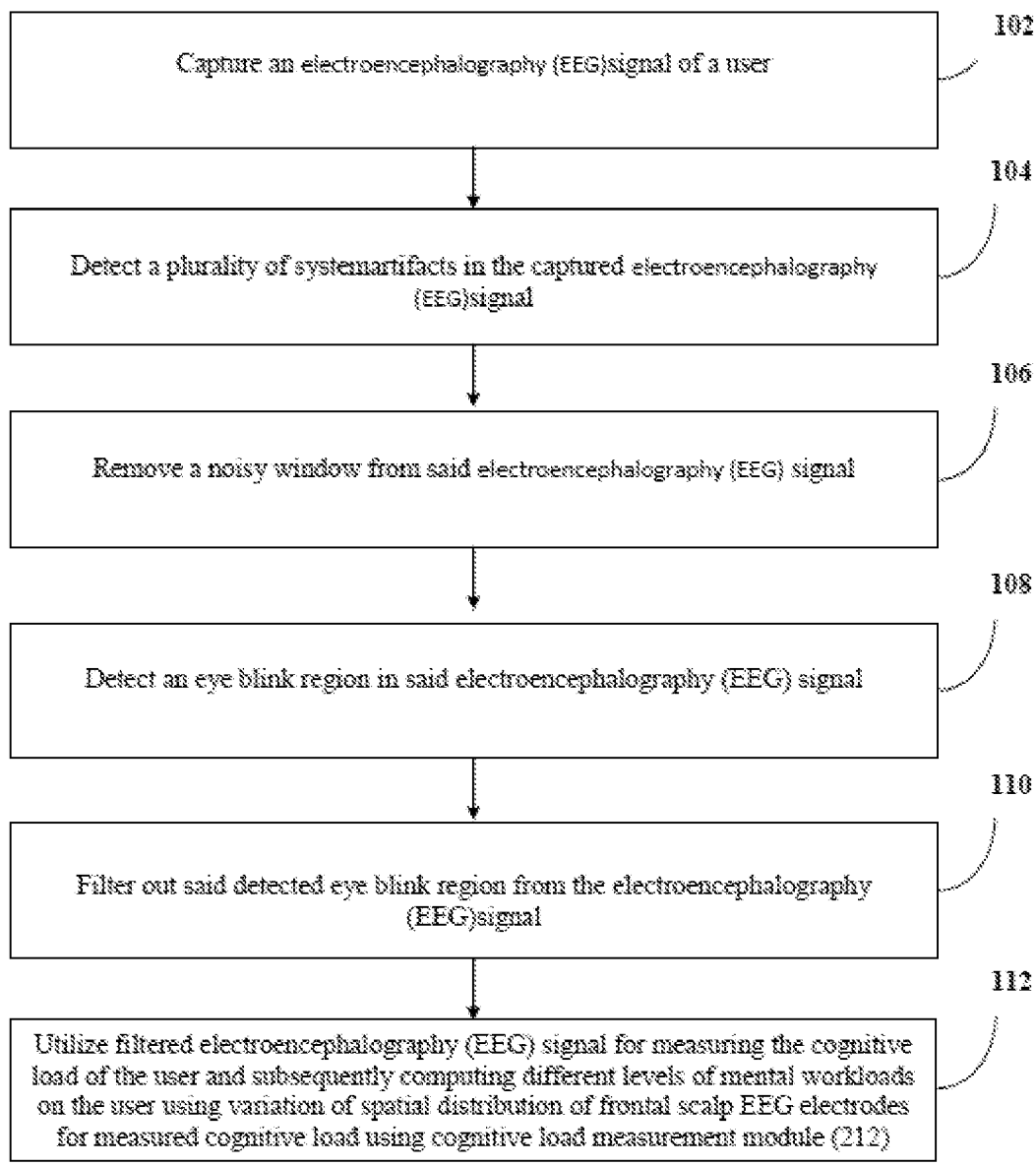
FIG. 1: shows a flow chart illustrating a processor implemented method for pre-processing of an electroencephalography signal of a user for cognitive load measurement.

Some embodiments of this invention, illustrating all its features, will now be discussed in detail.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present invention, the preferred, systems and methods are now described.

The disclosed embodiments are merely exemplary of the invention, which may be embodied in various forms.

The elements illustrated in the Figures inter-operate as explained in more detail below. Before setting forth the detailed explanation, however, it is noted that all of the discussion below, regardless of the particular implementation being described, is exemplary in nature, rather than limiting. For example, although selected aspects, features, or components of the implementations are depicted as being stored in memories, all or part of the systems and methods consistent with the attrition warning system and method may be stored on, distributed across, or read from other machine-readable media.

The techniques described above may be implemented in one or more computer programs executing on (or executable by) a programmable computer including any combination of any number of the following: a processor, a storage medium readable and/or writable by the processor (including, for example, volatile and non-volatile memory and/or storage elements), plurality of input units, and plurality of output devices. Program code may be applied to input entered using any of the plurality of input units to perform the functions described and to generate an output displayed upon any of the plurality of output devices.

Each computer program within the scope of the claims below may be implemented in any programming language, such as assembly language, machine language, a high-level procedural programming language, or an object-oriented programming language. The programming language may, for example, be a compiled or interpreted programming language. Each such computer program may be implemented in a computer program product tangibly embodied in a machine-readable storage device for execution by a computer processor.

Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as biological hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an biological disk (not shown) or a removable disk.

Any data disclosed herein may be implemented, for example, in one or more data structures tangibly stored on a non-transitory computer-readable medium. Embodiments of the invention may store such data in such data structure(s) and read such data from such data structure(s).

Referring to FIG. 1 is a flow chart illustrating a method for pre-processing of an electroencephalography signal of a user cognitive load measurement.

The process starts at step 102, wherein the electroencephalography signal of a user is captured. At the step 104, the plurality of system artifacts are detected in the captured electroencephalography signal. At the step 106, the noisy window from the captured electroencephalography signal is removed. At the step 108, an eye blink region from the captured electroencephalography signal is detected. At the step 110, the said detected eye blink region from the captured electroencephalography signal is filtered out and the process ends at the step 112, where the filtered electroencephalography signal is used for measuring the cognitive load of the user and subsequently computing different levels of mental workloads on the user using variation of spatial distribution in the frontal scalp EEG electrodes of measured cognitive load.

Figure 2:
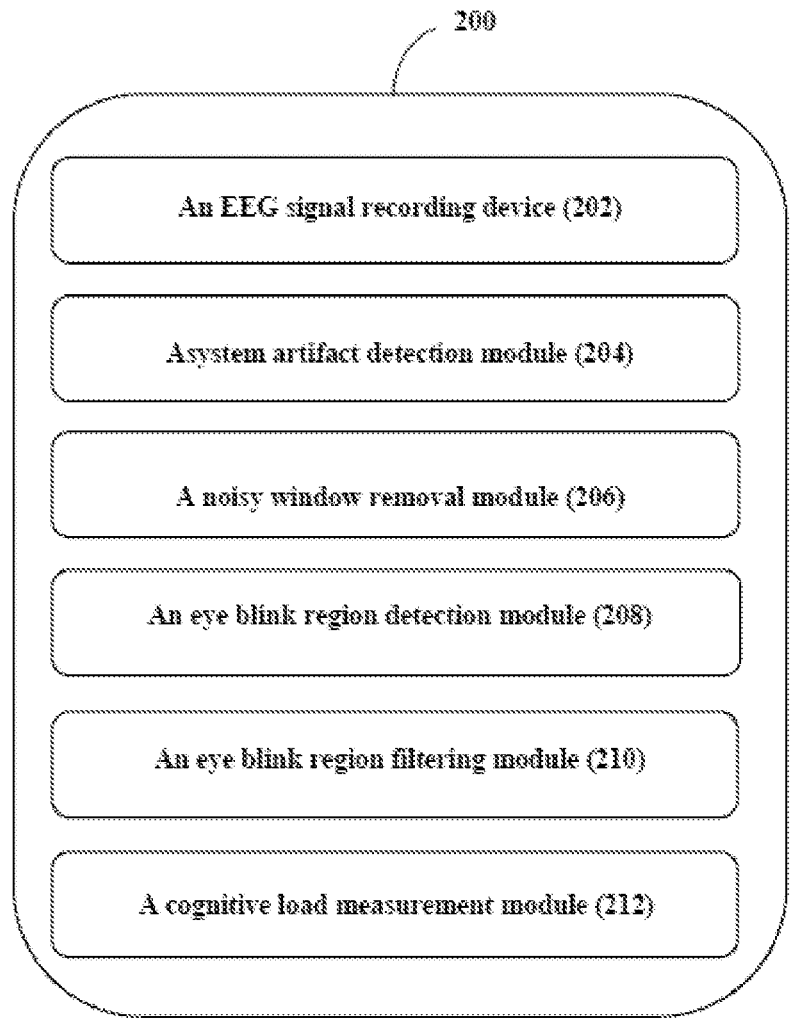
FIG. 2: shows a block diagram illustrating system architecture for pre-processing of an electroencephalography signal of a user for cognitive load measurement.

Referring to FIG. 2 is a block diagram illustrating system architecture for pre-processing of an electroencephalography signal of a user for cognitive load measurement.

In an embodiment of the present invention, a system (200) is provided for pre-processing of an electroencephalography signal of a user for cognitive load measurement.

The system (200) comprises of an electroencephalography signal recording device (202); a system artifact detection module (204); a noisy window removal module (206); an eye blink region detection module (208); an eye blink region filtering module (210); and a cognitive load measurement module (212).

In another embodiment of the present invention, the system (200) may be used for detecting the accuracy of the cognitive load by pre-processing the electroencephalography signal and removing the plurality of system artifacts, on the user, corresponding to the stimulus. In order to evaluate the cognitive load by pre-processing the electroencephalography signal and removing the plurality of system artifacts, the system (200), at first, receives electroencephalography signal of the user. Specifically, in the present implementation, the electroencephalography signal data is received by the electroencephalography signal recording device (202).

In another embodiment of the present invention, the EEG data may be recorded using 14-channel wireless Emotiv neuro headset. The EEG device may be worn on head of the user to receive EEG signal. The EEG data represents the EEG signal generated corresponding to the stimulus of the user.

In another embodiment of the present invention, an artifact detection module (204) is adapted for detecting plurality of system artifacts, wherein the system artifacts is selected from a group comprising but not limited to power supply interference, impedance fluctuations, spurious noise due to Bluetooth connectivity, electrical noise.

In another embodiment of the present invention, a noisy window removal module (206) is adapted for detecting and removing a noisy window from the captured electroencephalography signal. The module may further utilize a plurality of noisy window removal techniques a SDK based approach, Standard deviation (STD) based approach and skewness based approach.

In another embodiment of the present invention, a SDK based approach is used on Emotiv device. The Emotiv provides "SignalQuality" API which have been used to log the signal qualities. The API gives an indication of the noise levels of the raw EEG signal. There are five levels of the signal quality namely, "No signal", Very poor signal", "Poor signal", "Fair signal" and "Good signal". These levels are indicated as part of the metadata associated with each of the channels of the Emotiv device. The EEG signals are considered as noise free for which all the channels of the EEG device give "Good signal" as metadata.

In another embodiment of the present invention, a Standard Deviation based measurement is used to identify the noisy window. The EEG signal is subdivided into non-overlapped windows and then standard deviation S of the signal amplitude, is calculated for each window using equation 1. If S is found to be greater than the predefined threshold ($\tau_1$), then the corresponding window is treated as a noisy window. The higher the threshold better is the recall and lower the threshold better is the precision in detection of the noisy window. Hence, there is a tradeoff between the recall and the precision based on the setting of the threshold.

$$S = \sqrt{\frac{1}{N-1}\sum_{i=1}^{N} |A_i - \mu|^2} \quad (1)$$

where $A_i$ are the raw EEG samples, $\mu$ is the mean over all the $A_i$ and N is the number of samples in the window.

In another embodiment of the present invention, a signal skewness measurement gives a measure of lack of symmetry in the signal and used for identify noisy windows. The EEG signal is divided into non-overlapped windows and the signal skewness is calculated using equation 2.

$$S_n = \frac{E(x-\mu)^3}{\sigma^3} \quad (2)$$

where, x is the raw EEG signal in a window, $\mu$ is the mean and $\sigma$ is the standard deviation of the signal in the window, and E (.) denotes the expectation operator. If $S_n$ is less than a predefined threshold ($\tau_2$), then that particular window is treated as the noisy window. The higher the threshold better is the precision and lower the threshold better is the recall in detection of the noisy window. Hence there is a tradeoff between the recall and the precision based on the setting of the threshold.

In another embodiment of the present invention, an eye blink region detection module (208) is adapted for detecting and removing an eye blink region from the captured electroencephalography signal. The module may further utilize a plurality of technique for detecting and removing an eye blink, a SDK based, template based cross-correlation, auto-correlation based and a clustering based approach.

In another embodiment of the present invention, the SDK based detection is used in which the Emotiv provides "EE_Expressiv" API. The personalized training facility in Emotiv is required for certain applications. However, it is not user friendly to perform eye blink related trainings for each subject and thus without personalized training, the detection accuracy is quite less along with presence of false positives.

In another embodiment of the present invention, detection through template based cross-correlation is used in which one of the generic eye blink region is taken as the template (T). The raw EEG signal, x (n) is cross-correlated with T to generate the y (n) using equation 3. The length of the template is N. The cross-correlation is performed on each window of EEG signal (x) of length N, and a 50% overlap of windows is considered. If the output y(n) is above a predefined threshold ($\tau_3$), then the window is detected as having an eye blink.

$$y(n) = \sum_{m=0}^{N-1} x(n+m) * T(m) \quad (3)$$

In another embodiment of the present invention, detection through auto-correlation is used to overcome the limitation of the need for a generic eye blink template. It is based on the principle of detection of signal in multiple-input multiple-output wireless communication. The raw EEG signal, x(n) is auto-correlated with a time shifted version of x(n) for a window length of N to generate the y(n) using equation 4. If the output y(n) is above a predefined threshold ($\tau_4$), then the window is detected as having an eye blink.

$$y(n) = \sum_{m=0}^{N-1} x(n+m) * x(m) \quad (4)$$

In another embodiment of the present invention, detection through clustering based approach is used in which we sub divide the EEG signal into windows of duration 1 sec (with 50% overlap) and then calculate the delta band power (<4 Hz) for each window as the features. Finally a standard k-means algorithm is applied on the features. Depending on the blink strength, the delta power varies and hence a fixed number of clusters often miss the low strength blinks. Thus the number of clusters are varied from 2 to 5 and examined the value of K that gives minimum Xie-Beni index. The lowest value of Xie-Beni index indicates the best formation of clusters. The upper cutoff of 5 is decided based on experiments. Once the clusters are found for the best Xie-Beni index, the EEG data is extracted from the cluster corresponding to the maximum size conditioned to the lowest delta power and the data corresponding to the remaining clusters are marked as blink regions.

In another embodiment of the present invention, the filtering of eye blink region is done by passing the raw EEG signals through 0.5 Hz 256th order high pass FIR filter and a 4 Hz 640th order high pass FIR filter. Once the blink start and end regions were identified, 0.5 Hz high pass EEG signals were cleaned by replacing the data points in the eye blink region by the data corresponding to filtered output of 4 Hz high pass filter.

In another embodiment of the present invention, discrimination of cognitive load is measured by using stroop test from the cleaned EEG signal which is obtained by removing the noisy windows and filtering the eye blink regions. The discrimination of the cognitive load is measured for each lead/channel using a product of change in mean frequencies $(f_r(\alpha), f_r(\theta))$ and corresponding power $(|f_r(\alpha)|, |(f_r(\theta)|)$ for both alpha and theta band as shown in equation 5. The change is measured between the EEG signal for Stroop stimulus and the initial baseline data taken before the start of the experiment. The subjects are asked to relax during the initial baseline period.

$$L^i(t) = (\Delta |f_r^i(\alpha)| f_r^i(\alpha) - \Delta |f_r^i(\theta)|) \quad (5)$$

where i in the lead or channel index and $L^i(t)$ is the cognitive load for the ith channel, a discrimination index (DI) as the standard deviation of the cognitive load among the selected leads/channel as given in equation 6. The lead selection can be the four left frontal leads namely, AF3, F7, F3, FC5 of the device.

$$DI = std_i(L^i(t)), i \in \{AF3, F7, F3, FC5\} \quad (6)$$

where $std_i$ is the standard deviation of the cognitive load among all the four leads i.

For low cognitive load, the area under the standard deviation curve is found to be greater compared to that for high cognitive load.

In one exemplary embodiment, a group of 17 participants, are selected in the age group of 25-32 years. They were right handed male engineers working in research lab (Innovation Lab, TCS). They have either normal vision or corrected to normal 6/6 vision with spectacles. These ensure that we have minimum variance in the expertise level and brain lateralization across all the participants. Each of the people were said to read the colours while wearing the EEG headset. In one type, the name of the colour and the font colour are different; i.e. RED is written in blue color and in the second type both are same, i.e. RED is written in red colour. The cognitive load is higher as the name of the colour and the font colour are different, whereas the cognitive load is less when both name and colour are same.

A low resolution EEG device for the data collection, namely, 14 channel neuro headset from Emotiv is used to analyze the effects of different eye blink removal techniques for low resolution devices. The common mode sense (CMS) and driven right leg (DRL) reference electrodes, placed in P3 and P4 location were used as the ground electrodes. The device follows the standard 10-20 electrode system for channel locations. The sampling rate for Emotiv device is 128 Hz. An in-house Python based tool is developed for synchronized capture of (i) raw EEG data, (ii) associated SDK provided parameters, along with (iii) a webcam video capture for the subject, while presenting the stimulus/task on the computer screen. The webcam video was used for generating the ground truth for the eye-blink regions. The capture tool was equipped to introduce markers (baseline start/end, stimulus start/end etc.) in the EEG data while collecting the same.

At the start of the experiment, a fixation cross is shown on the screen for a duration of 5 sec. During this time, the participants were asked to concentrate on the cross. After that a Stroop slide (either high/low) was presented. Next another 5 sec. relaxation time was given. Finally another Stroop slide was presented. The duration for which the Stroop slides were shown was treated as the trial intervals. For each participant two trial sessions were conducted. In one session high Stroop slide was followed by low Stroop slide. In the other session reverse order was followed. For half of the participants, high level Stroop was presented first followed by the low level Stroop slide. The order was reversed for the remaining participants.

During the synthetic data collection, participants were asked to blink after a certain interval of time (after 5 sec. or 10 sec. etc) while wearing the Emotiv device. Natural blink data are collected from 12 participants and synthetic data from 5 participants. The average duration of the synthetic blink files was 60.07 sec.

Based on the data captured from the above example, the single metric F1 score was calculated which is the harmonic mean of precision and recall as shown in eq.(7).

$$F1 = \frac{2 * \text{precision} * \text{recall}}{\text{precision} + \text{recall}} \quad (7)$$

A noisy window removal module (206) is adapted for detecting and removing a noisy window from the captured electroencephalography signal. The module may further utilize a plurality of noisy window removal techniques a SDK based approach, Standard deviation (STD) based approach and skewness based approach. The thresholds selected for the skewness was 0.5 and STD was 50. Then F1 score, as mentioned in table 1, was calculated based on the equation 7 and the performance of the SDK is not at all reliable and the skewness based noise detection was the best among the three methods.

TABLE 1

| | Detection method | | |
|---|---|---|---|
| | SDK | Skewness | STD |
| F1 score | 0.05 | 0.46 | 0.295 |

An eye blink region detection module (208) is adapted for detecting and removing an eye blink region from the captured electroencephalography signal. The module may further utilize a plurality of technique for detecting and removing an eye blink, a SDK based, template based cross-correlation, auto-correlation based and a clustering based approach. The duration of the eye blink ranges from 100 msec to 600 msec or more, the window size was considered as 1 second with 50% overlap. In case of auto-correlation the shift in the signal was given as 50 samples (approximately 400 msec at 128 Hz sampling rate for Emotiv). The amount of shift was derived experimentally which is expected to be quite less than the duration of the eye blink.

Figure 3:
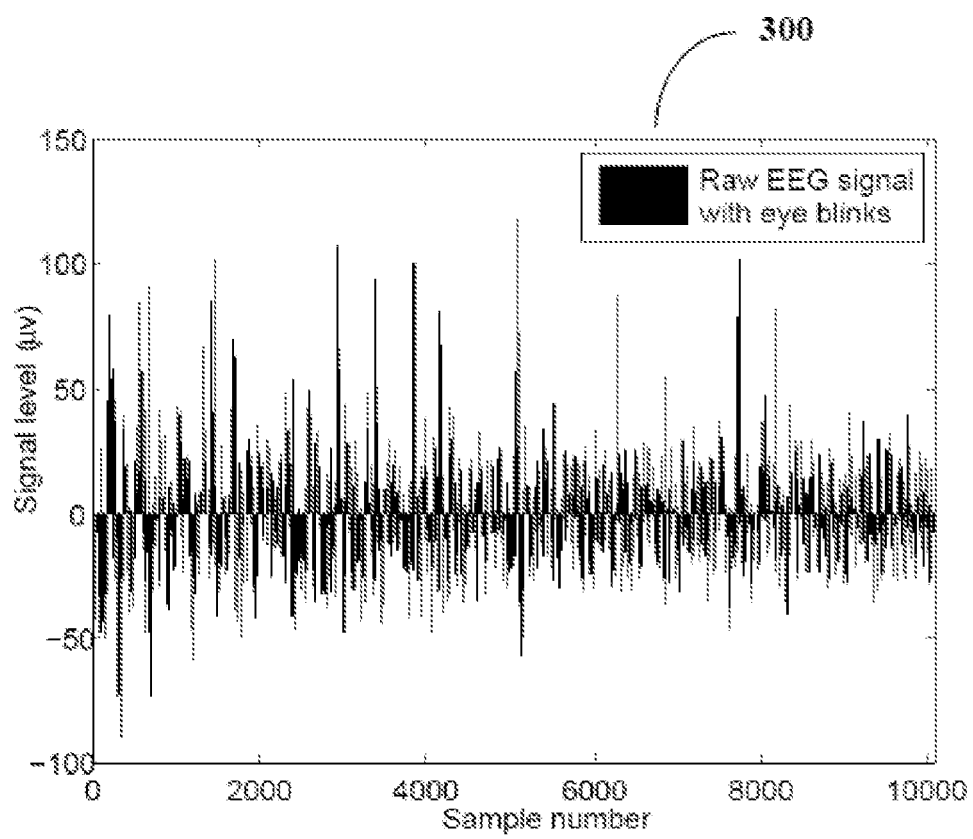
FIG. 3: shows a graph illustrating raw EEG signal with eye-blinks.
Figure 4:
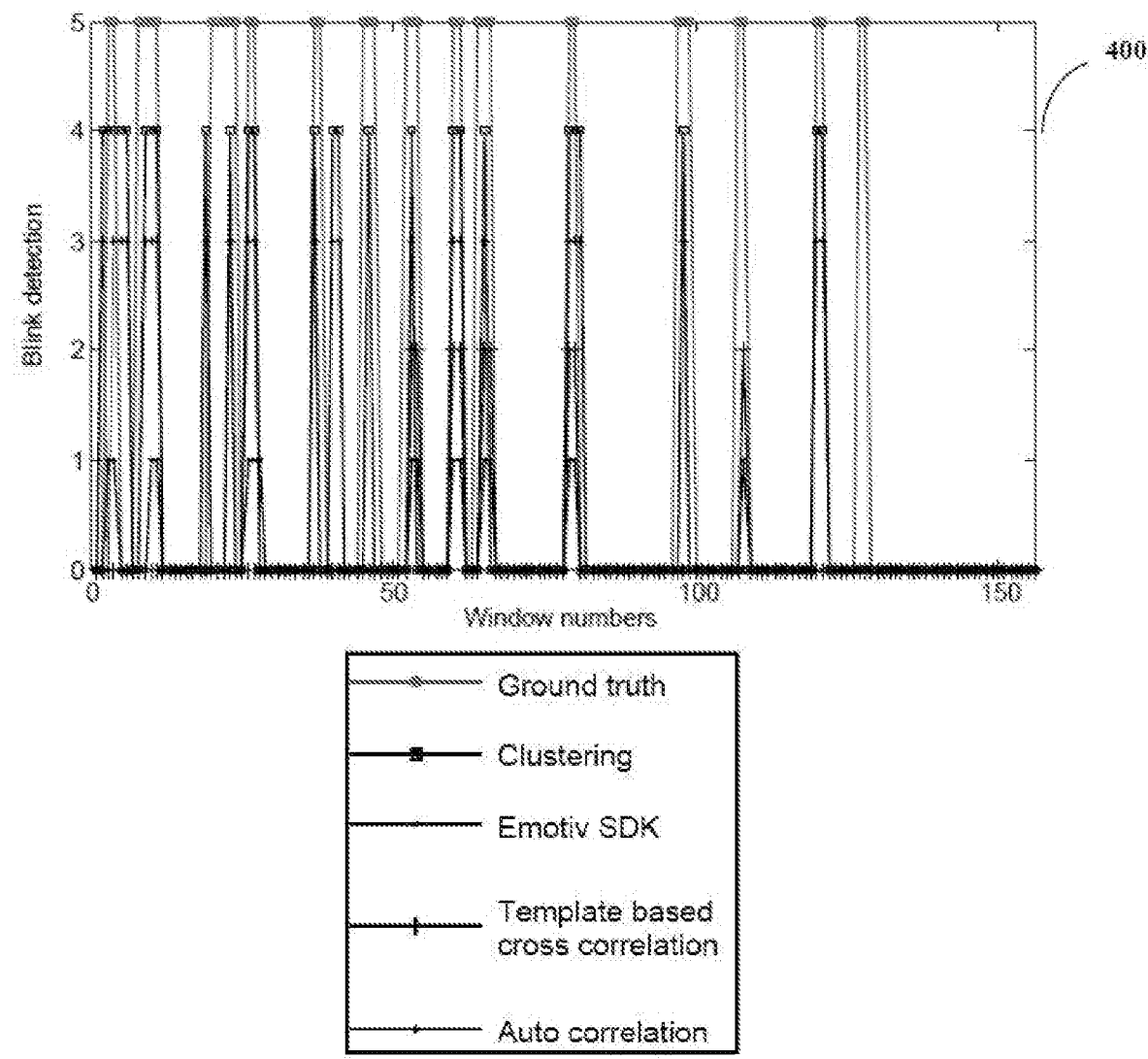
FIG. 4: shows a graph illustrating detected eye-blinks with various methods.

A sample raw EEG signal is shown in FIG. 3. The FIG. 3 shows a graph (300) illustrating raw EEG signal with eye-blinks. The high amplitude spikes with signal level close to 100 μV indicate the presence of eye-blink. FIG. 4 shows a graph (400) illustrating detected eye-blinks with various methods. The FIG. 4 shows the comparison of the detection of eye-blinks using different methods in comparison with the ground truth for the EEG signal shown in FIG. 3. The horizontal axis of FIG. 4 represents the window number where length of each window corresponds to 64 samples of EEG signal. In order to pictorially represent the comparison, the detection of various methods at 5 different levels namely, Emotiv SDK as level 1, template based cross-correlation as level 2, auto-correlation as level 3, clustering as level 4 and ground truth as level 5 was carried. The value of zero indicates no blink where as any other value indicates blink detection with the method specified as that level and comparison of various types of eye blink detection techniques for synthetic blinks are shown in table 2 and for natural blinks in table 3.

TABLE 2

| Detection method | Average Precision | Average Recall | F1 Score |
| --- | --- | --- | --- |
| SDK based detection | 0.72 | 0.6 | 0.65 |
| Template based cross-correlation | 1 | 0.69 | 0.82 |
| Auto correlation based method | 0.78 | 1 | 0.876 |
| Clustering based method | 0.96 | 0.93 | 0.945 |

TABLE 3

| Detection method | Average Precision | Average Recall | F1 Score |
| --- | --- | --- | --- |
| SDK based detection | 0.79 | 0.88 | 0.83 |
| Template based cross-correlation | 0.83 | 0.72 | 0.77 |
| Auto correlation based method | 0.93 | 0.92 | 0.925 |
| Clustering based method | 0.93 | 0.93 | 0.93 |

After the removal of noisy windows, once the blink start and end indices are correctly detected, then the filtering technique is applied and the discrimination index (DI) in terms of normalized STD for 17 sessions was computed. The STD was on the lower side for the high load Stroop stimulus and on the higher side for the low load Stroop stimulus.

Figure 5:
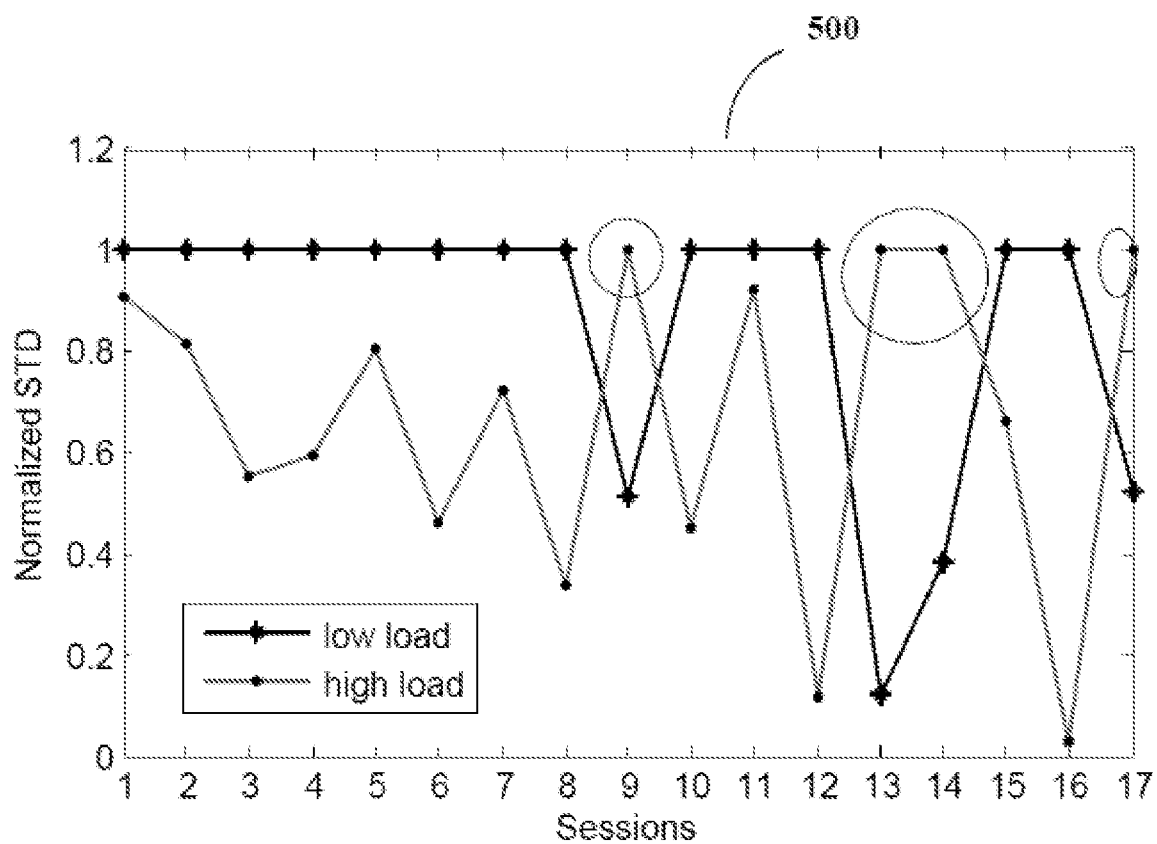
FIG. 5: shows a graph illustrating normalized STD for low and high Stroop color test.

FIG. 5 shows a graph (500) illustrating normalized STD for low and high Stroop color test. The FIG. 5 shows that for high load, most of the left brain regions were equally loaded and the spatial variation among that region (AF3, F7, F3 and FC5) was less. Thus it can be seen that for 13 sessions among 17, the normalized STD of the cognitive load was able to discriminate successfully among the low and high mental work load. The unsuccessful ones are marked with circles. The same experiment was done without pre-processing where 11 sessions were correctly discriminated. Thus there is an improvement of 11.7% i.e. ((13-11)*100/17) in the detection accuracy.

Figure 6:
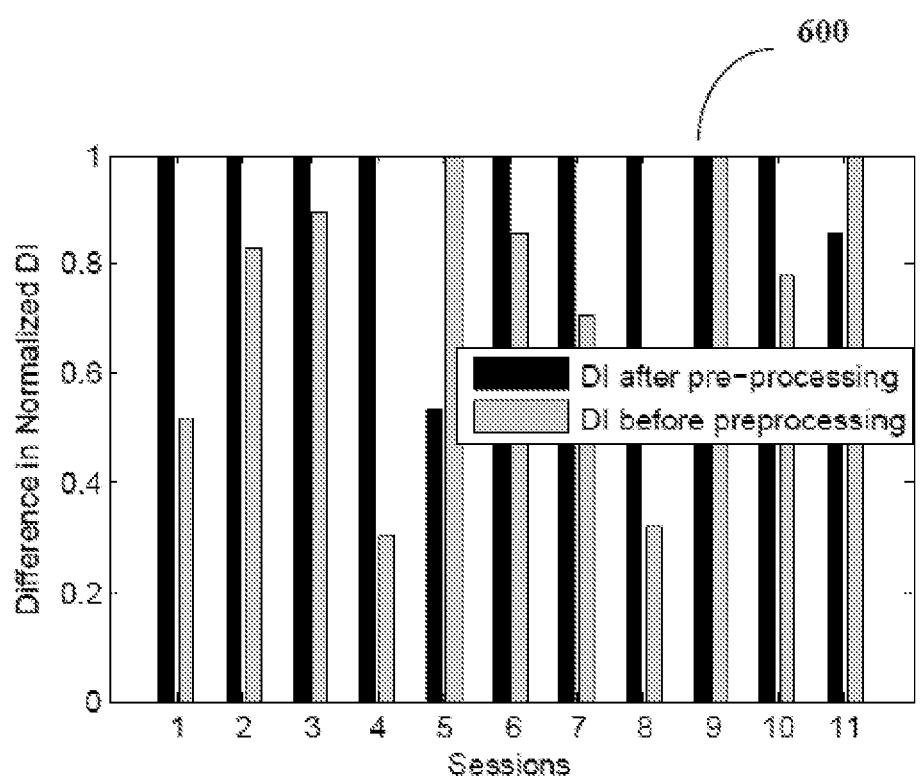
FIG. 6: shows a graph illustrating improvement in the normalized discrimination index for low and high stroop color test after pre-processing of the signal.

The improvement in terms of the difference in DI among the low and high load on pre-processed and raw EEG signal was compared for 11 sessions. FIG. 6 shows a graph (600) illustrating improvement in the normalized discrimination index for low and high stroop color test after pre-processing of the signal. The FIG. 6 shows the bar plot of difference in normalized DI for before and after the pre-processing. The normalized DI after the pre-processing was higher than that before pre-processing, indicating the improvement in the discrimination power.

In view of the foregoing, it will be appreciated that the present invention provides a method and system for pre-processing of the electroencephalography signal of a user cognitive load measurement by monitoring the mental activity of the user. Still, it should be understood that the foregoing relates only to the exemplary embodiments of the present invention, and that numerous changes may be made thereto without departing from the spirit and scope of the invention as defined by the following claims.

We claim:

1. A method for pre-processing of an electroencephalography (EEG) signal of a user for cognitive load measurement, said method comprising processor implemented steps of:
   a) capturing the electroencephalography signal of the user using an electroencephalography signal recording device (202), wherein the electroencephalography signal is generated corresponding to a stroop stimulus, wherein the electroencephalography signal is a low resolution electroencephalography signal, and wherein the electroencephalography signal recording device is a low resolution device;
   b) detecting a plurality of system artifacts in the captured electroencephalography signal using an artifact detection module (204);
   c) removing a noisy window from said electroencephalography signal using a noisy window removal module (206), wherein the noisy window is removed by detecting the noisy window using a signal skewness measurement, wherein the signal skewness measurement of the electroencephalography signal is measured by sub-dividing the electroencephalography signal into non overlapping windows, and wherein a non overlapping window is detected as the noisy window if the measured signal skewness measurement is less than a predefined threshold;
   d) detecting an eye blink region in said electroencephalography signal using an eye blink region detection module (208), wherein the eye blink region is detected using a clustering based method, the clustering based method comprising steps of:
      sub-dividing the electroencephalography signal into overlapping windows, wherein each window of the overlapping windows has a windows size of one second;
      calculating a delta band power for each window of the overlapping windows as features;
      applying a standard k-means algorithm on the features;
      varying number of clusters and examining value of k that gives minimum Xie-Beni index, wherein the Xie-Beni index indicates finest formation of clusters; and
      extracting electroencephalography data from a cluster corresponding to maximum size conditioned to lowest delta band power and marking data corresponding to remaining clusters as eye blink regions;
   e) filtering out said detected eye blink region from the electroencephalography signal using an eye blink region filtering module (210); and
   f) utilizing the filtered electroencephalography signal to measure discrimination of the cognitive load as a high mental workload or a low mental workload, among selected channels of the user and subsequently calculating different levels of mental workloads on the user using variation of spatial distribution of frontal scalp EEG electrodes for measured cognitive load using cognitive load measurement module (212), wherein the cognitive load for each channel is obtained using a product of change in mean frequencies and corresponding power for both alpha and theta band, the change measured between the filtered electroencephalography signal for stroop stimulus and initial baseline data, and wherein the discrimination of the cognitive load is obtained as a standard deviation of the cognitive load among the selected channels.

2. The method of claim 1, wherein the plurality of system artifacts includes artifacts pertaining to said electroencephalography signal recording device (202).

3. The method of claim 2, wherein the plurality of system artifacts pertaining to said electroencephalography signal recording device (202) is selected from a group comprising of power supply interference, an impedance fluctuation, a spurious noise and an electrical noise and a combination thereof.

4. The method of claim 1, further comprises of indicating a noise level of the noisy window of said electroencephalography signal, wherein the noise level of the noisy window is selected from a group comprising of no signal, very poor signal, poor signal, fair signal and good signal.

5. The method of claim 1, wherein the eye blink region is filtered out from the electroencephalography signal using selective high pass filters.

6. The method of claim 1, wherein the discrimination of cognitive load is between at least two levels of measured cognitive load of the user.

7. A system (200) for pre-processing of an electroencephalography signal of a user for cognitive load measurement, the system (200) comprising:
a) a processor;
b) a memory coupled to said processor, the processor configured to perform steps of:
capturing the electroencephalography signal of the user, wherein the electroencephalography signal is generated corresponding to a stroop stimulus, wherein the electroencephalography signal is a low resolution electroencephalography signal;
detecting a plurality of system artifacts in the captured electroencephalography signal;
removing a noisy window from said electroencephalography signal, wherein the noisy window is removed by detecting the noisy window using a signal skewness measurement, wherein the signal skewness measurement of the electroencephalography signal is measured by subdividing the electroencephalography signal into non overlapping windows, and wherein a non overlapping window is detected as the noisy window if the measured signal skewness measurement is less than a predefined threshold;
detecting an eye blink region in said electroencephalography signal, wherein the eye blink region is detected using a clustering based method, the clustering based method comprising steps of:
sub-dividing the electroencephalography signal into overlapping windows, wherein each window of the overlapping windows has a windows size of one second;
calculating a delta band power for each window of the overlapping windows as features;
varying number of clusters and examining value of k that gives minimum Xie-Beni index, wherein the Xie-Beni index indicates finest formation of clusters; and
extracting electroencephalography data from a cluster corresponding to maximum size conditioned to lowest delta band power and marking data corresponding to remaining clusters as eye blink regions;
filtering out said detected eye blink region from the electroencephalography signal for measuring the cognitive load of the user; and
utilizing the filtered electroencephalography signal to measure discrimination of the cognitive load as a high mental workload or a low mental workload, among selected channels of the user and subsequently calculating different levels of mental workloads on the user using variation of spatial distribution of frontal scalp EEG electrodes for measured cognitive load, wherein the cognitive load for each channel is obtained using a product of change in mean frequencies and corresponding power for both alpha and theta band, the change measured between the filtered electroencephalography signal for stroop stimulus and initial baseline data, and wherein the discrimination of the cognitive load is obtained as a standard deviation of the cognitive load among the selected channels.

8. The system of claim 7, wherein the eye blink region is filtered out from the electroencephalography signal using selective high pass filters.

9. The system of claim 7, wherein the plurality of system artifacts includes artifacts pertaining to an electroencephalography signal recording device (202).

10. The system of claim 9, wherein the plurality of system artifacts pertaining to said electroencephalography signal recording device (202) is selected from a group comprising of power supply interference, an impedance fluctuation, a spurious noise and an electrical noise and a combination thereof.

* * * * *